(12) United States Patent
Krokoszinski et al.

(10) Patent No.: US 9,035,110 B2
(45) Date of Patent: May 19, 2015

(54) PROCESS FOR HEAT INTEGRATION IN THE HYDROGENATION AND DISTILLATION OF $C_3$—$C_{20}$-ALDEHYDES

(71) Applicant: BASF SE, Ludwigshafen (DE)

(72) Inventors: Roland Krokoszinski, Weisenhein a.Berg (DE); Karl-Heinz Walczuch, Ludwigshafen (DE)

(73) Assignee: BASF SE (DE)

( * ) Notice: Subject to any disclaimer, the term of this patent is extended or adjusted under 35 U.S.C. 154(b) by 69 days.

(21) Appl. No.: 13/786,678

(22) Filed: Mar. 6, 2013

(65) Prior Publication Data

US 2013/0237726 A1    Sep. 12, 2013

Related U.S. Application Data

(60) Provisional application No. 61/607,610, filed on Mar. 7, 2012.

(51) Int. Cl.
*C07C 29/14* (2006.01)
*C07C 29/141* (2006.01)
*C07C 29/17* (2006.01)

(52) U.S. Cl.
CPC .............. *C07C 29/141* (2013.01); *C07C 29/175* (2013.01)

(58) Field of Classification Search
CPC ........ C07C 33/02; C07C 29/00; C07C 29/40; C07C 29/47; C07C 29/80; C07C 29/90; C07C 29/141

USPC ......... 568/840, 876, 878, 880, 881, 884, 913, 568/914

See application file for complete search history.

(56) References Cited

U.S. PATENT DOCUMENTS

| 4,009,124 A | 2/1977 | Laurer et al. |
| 4,451,677 A * | 5/1984 | Bradley et al. ................. 568/881 |
| 2002/0019574 A1 * | 2/2002 | Ueda et al. ..................... 568/880 |
| 2003/0114720 A1 | 6/2003 | Hoffmann et al. |

FOREIGN PATENT DOCUMENTS

| CA | 1072123 A1 | 2/1980 |
| DE | 2445303 A1 | 4/1976 |
| DE | 2628987 A1 | 1/1978 |
| DE | 3228881 A1 | 2/1984 |
| WO | WO-01/87809 A1 | 11/2001 |

* cited by examiner

*Primary Examiner* — Sudhakar Katakam
(74) *Attorney, Agent, or Firm* — Drinker Biddle & Reath LLP

(57) ABSTRACT

The present invention relates to a process for heat integration in the preparation of saturated $C_3$-$C_{20}$-alcohols, in which a hydrogenation feed comprising at least one $C_3$-$C_{20}$-aldehyde is hydrogenated in the presence of a hydrogen-comprising gas in a hydrogenation zone and a discharge is taken off from the hydrogenation zone and subjected to distillation in at least one distillation column to give a fraction enriched in saturated $C_3$-$C_{20}$-alcohols.

14 Claims, No Drawings

PROCESS FOR HEAT INTEGRATION IN THE HYDROGENATION AND DISTILLATION OF $C_3$—$C_{20}$-ALDEHYDES

CROSS-REFERENCE TO RELATED APPLICATIONS

This application claims the benefit of U.S. Provisional Application No. 61/607,610, filed Mar. 7, 2012, which is incorporated herein by reference.

The present invention relates to a process for heat integration in the preparation of saturated $C_3$-$C_{20}$-alcohols, in which a hydrogenation feed comprising at least one $C_3$-$C_{20}$-aldehyde is hydrogenated in the presence of a hydrogen-comprising gas in a hydrogenation zone and a discharge is taken off from the hydrogenation zone and subjected to distillation in at least one distillation column to give a fraction enriched in saturated $C_3$-$C_{20}$-alcohols.

The catalytic hydrogenation of aldehydes to obtain alcohols is an industrial process which has been practiced for decades and in which a number of catalysts which generally comprise elements of groups VI to VIII and transition group I of the Periodic Table, in particular the elements chromium, manganese, iron, cobalt, nickel and/or copper are used. Such catalysts are described, for example, in DE-A 32 28 881, DE-A 26 28 987 and DE-A 24 45 303. The alcohols prepared by these processes are used widely, e.g. as solvents or as plasticizer alcohols.

The hydroformylation of propene results in an n-butyraldehyde/isobutyraldehyde-comprising mixture which can be subjected to further processing to give a plurality of products of value. The n-butyraldehyde/isobutyraldehyde-comprising mixture can, optionally after separation into n-butyraldehyde and isobutyraldehyde by distillation, be subjected to hydrogenation to give n-butanol and isobutanol. The alcohols are generally additionally subjected to purification by distillation.

n-Butyraldehyde is also an important intermediate in the preparation of 2-ethylhexanol by aldol addition, dehydration and hydrogenation. Here, the "aldol condensation", i.e. the combination of aldol addition to form the β-hydroxyaldehyde adduct and subsequent elimination of water to form the α,β-unsaturated aldehydes concerned, will also be referred to as "enalization" in the following.

2-Ethylhexanol (2-EH) is employed, inter alia, for preparing phthalate plasticizers and acrylate esters which are used in adhesives and surface coatings such as acrylic paints or printing inks and as impregnates.

The hydrogenation of lower aldehydes is an exothermic reaction. To remove the heat of reaction, the reaction mixture therefore has to be subjected to cooling, e.g. by passing it through a heat exchanger and transferring the heat of reaction to a cooling medium, e.g. a stream of cooling water or air.

In the hydrogenation of aldehydes, in particular at high hydrogenation temperatures, various undesirable secondary reactions such as acetalization or aldolization, the Tishchenko reaction or ether formation proceed alongside the desired hydrogenation of the aldehyde to form the alcohol. The hydrogenation product is therefore generally subjected to a work-up, e.g. a single-stage or multistage distillation, in order to obtain the alcohol concerned in the desired purity. In the fractional distillation of the crude alcohol from the aldehyde hydrogenation, the reaction mixture is vaporized at the bottom of the distillation column(s) and recondensed at the top. The vaporization energy supplied to the bottom is removed again at the top by means of heat exchangers, with water or air usually being used as cooling medium, as in the hydrogenation.

WO 01/87809 describes a process for preparing saturated $C_3$-$C_{20}$-alcohols, in which a liquid hydrogenation feed comprising at least one $C_3$-$C_{20}$-aldehyde is passed in the presence of a hydrogen-comprising gas over a bed of a hydrogenation catalyst, with a quantity of a salt-like base which is homogeneously soluble in the hydrogenation feed being added to the hydrogenation feed. The addition of the base suppresses secondary reactions such as acetalization, aldolization, the Tishchenko reaction or ether formation. The hydrogenation product can be subjected to fractional distillation.

The known processes for preparing saturated alcohols by hydrogenation of the corresponding aldehydes and subsequent distillation of the crude alcohol mixture are capable of improvement in terms of their energy efficiency. If energy is merely transferred to a cooling medium in the cooling of the hydrogenation reaction and/or the condensation of the overhead product from the distillation and discharged from the process, a large quantity of energy is not utilized and is lost. However, even use of a classical integrated heat system in which the heat of hydrogenation and/or the heat of condensation is transferred to a heat transfer medium in a first heat exchanger and after transport to the site of an energy-consuming process is transferred to a stream in this process in a second heat exchanger is still capable of improvement.

It is an object of the present invention to provide a process for preparing saturated $C_3$-$C_{20}$-alcohols from $C_3$-$C_{20}$-aldehydes in which the heat of hydrogenation and/or the heat of condensation obtained in the distillation of the alcohols can be removed effectively and simply and reused with the highest possible energy utilization.

This object is achieved according to the invention by a process for heat integration in the preparation of saturated $C_3$-$C_{20}$-alcohols, in which a hydrogenation feed comprising at least one $C_3$-$C_{20}$-aldehyde is hydrogenated in the presence of a hydrogen-comprising gas in a hydrogenation zone and a discharge is taken off from the hydrogenation zone and subjected to distillation in at least one distillation column to give a fraction which is enriched in saturated $C_3$-$C_{20}$-alcohols, wherein a liquid stream S1) is taken off from the hydrogenation zone, heat is withdrawn from this stream and the stream is subsequently recirculated to the hydrogenation zone and/or a gaseous stream S2) is taken off at the top of at least one of the distillation columns, heat is withdrawn from this stream and the stream is optionally then recirculated to the distillation, where the heat is withdrawn from the stream S1) and/or the stream S2) by indirect heat exchange and is transferred to a stream to be heated without the use of an auxiliary medium for heat transfer.

A specific embodiment of the invention is a process for heat integration in the preparation of n-butanol and/or isobutanol, in which a) an n-butyraldehyde/isobutyraldehyde mixture is subjected to fractional distillation to give a fraction comprising the major part of the n-butyraldehyde and a fraction comprising the major part of the isobutyraldehyde, b1) the stream comprising the major part of the n-butyraldehyde from step a) is subjected to hydrogenation in the presence of hydrogen in a hydrogenation zone H1), c1) optionally, a liquid stream S1c1) is taken off from the hydrogenation zone H1), heat is withdrawn from this stream by passing it together with the n-butyraldehyde/ isobutyraldehyde mixture to be fractionated in step a) through a heat exchanger and subsequently recirculating the stream to the hydrogenation zone H1), d1) a discharge is taken off from the hydrogenation zone H1) and subjected to distillation in at least one distillation column to give a fraction enriched in n-butanol, e1) optionally, a gaseous stream S2e1) is taken off at the top of at least one of the distillation columns, heat is withdrawn from this stream by passing it together with the n-butyraldehyde/isobutyraldehyde mixture to be fractionated in step a) through a heat exchanger and optionally then recirculating the stream to the distillation, and/or 2) the stream comprising the major part of the isobutyraldehyde from step a) is subjected to hydrogenation in the presence of hydrogen in a hydrogenation zone H2), c2) optionally, a liquid stream S1c2) is taken off from the hydrogenation zone H2), heat is withdrawn from this stream by passing it together with the n-butyraldehyde/isobutyraldehyde mixture to be fractionated in step a) through a heat exchanger and subsequently recirculating the stream to the hydrogenation zone H2), d2) a discharge is taken off from the hydrogenation zone H2) and subjected to distillation in at least one distillation column to give a fraction enriched in isobutanol, e2) optionally, a gaseous stream S2e2) is taken off at the top of at least one of the distillation columns, heat is withdrawn from this stream by passing it together with the n-butyraldehyde/isobutyraldehyde mixture to be fractionated in step a) through a heat exchanger and optionally then recirculating the stream to the distillation, with the proviso that at least one of the steps c1), e1), c2) or e2) is necessarily provided.

In a further specific embodiment, the process for heat integration according to the invention comprises the following steps:

provision of at least one n-butyraldehyde/isobutyraldehyde mixture by hydroformylation of a propene-comprising starting material, fractional distillation of the n-butyraldehyde/isobutyraldehyde mixture to give a fraction comprising the major part of the n-butyraldehyde and a fraction comprising the major part of the isobutyraldehyde, division of the fraction comprising the major part of the n-butyraldehyde into two subfractions, hydrogenation of the first subfraction in the presence of a hydrogen-comprising gas in a hydrogenation zone and distillation of the discharge taken off from the hydrogenation zone in at least one distillation column to give a fraction enriched in n-butanol, subjecting of the second subfraction to an enalization reaction, catalytic hydrogenation of the product mixture obtained in the enalization reaction and distillation of the hydrogenation product to give a fraction enriched in 2-ethylhexanol, where a liquid stream S1) is taken off from the hydrogenation zone for the hydrogenation of the first subfraction, heat is withdrawn from this stream by passing it together with the n-butyraldehyde/isobutyraldehyde mixture to be fractionated through a heat exchanger and the stream is subsequently recirculated to the hydrogenation zone and/or a gaseous stream S2) is taken off at the top of at least one distillation column for the distillation of the discharge from the hydrogenation zone, heat is withdrawn from this stream by passing it together with the n-butyraldehyde/isobutyraldehyde mixture to be fractionated through a heat exchanger and the stream is optionally then recirculated to the distillation and/or a liquid stream S3) is taken off in the hydrogenation of the product of the enalization reaction and heat is withdrawn from this stream S3) by passing it together with the n-butyraldehyde/isobutyraldehyde mixture to be fractionated through a heat exchanger and the stream S3) is subsequently recirculated to the hydrogenation of the product of the enalization reaction.

Unless specifically stated otherwise, the following information in respect of suitable and preferred embodiments of the process of the invention for heat integration in the preparation of saturated $C_3$-$C_{20}$-alcohols applies to suitable and preferred embodiments of steps a), b1) to e1) and b2) to e2) of the process for heat integration in the preparation of n-butanol and/or isobutanol.

The process of the invention is preferably carried out continuously.

In indirect heat exchange, heat is transferred from a fluid having a relatively high temperature to a colder fluid via a wall which separates the liquid phases. To achieve indirect transfer of heat energy from one fluid stream to another, the two fluids can be passed through a heat exchanger. According to the invention, a conventional heat exchanger is used for indirect heat exchange. The local temperatures during heat exchange depend greatly on the direction of flow of the hot medium and the cold medium, with a distinction being made between three basic cases:

parallel flow or concurrent: hot and cold medium flow along the heat exchange surface in the same direction, countercurrent: hot and cold medium flow in opposite directions on the two sides of the wall dividing them, cross-current and transverse flow: the stream comprising the hot medium flows perpendicularly onto the dividing wall, i.e. transverse to the cold medium.

In addition, a series of combinations of these basic types is possible. Thus, cross-countercurrents in which the medium to be heated and the medium to be cooled are conveyed in a sinusoidal manner by means of deflection plates is frequently employed in shell-and-tube reactors.

Suitable heat exchangers are the customary apparatuses known to those skilled in the art in which heat is transferred from one medium to another. Typical embodiments of heat exchangers are condensers and evaporators. The heat exchangers used according to the invention can have the customary constructions, e.g. plate exchangers, ring groove exchangers, finned tube exchangers, lamella exchangers, double tube exchangers, shell-and-tube exchangers, split tube exchangers, disk exchangers, spiral exchangers, block exchangers, scraped exchangers, screw exchangers, helical exchangers, fluidized-bed exchangers, candle exchangers, cooled circulation exchangers and two- and three-tube coil exchangers.

In a preferred embodiment, the heat withdrawn from the stream S1) and/or S2) is used in a heat-consuming step of the process of the invention for preparing saturated $C_3$-$C_{20}$-alcohols. Such steps include not only the hydrogenation of at least one $C_3$-$C_{20}$-aldehyde and distillation of the discharge from the hydrogenation zone but also further preceding and/or subsequent reaction and/or work-up steps.

According to the invention, the streams S1), S2) and S3) are, if present, conveyed to the place where heat is consumed without the heat present therein being transferred to an auxiliary medium in between. This can, for example, be effected in conventional, optionally thermally insulated and/or pressure-rated pipes. A significant heat-consuming step of the process of the invention is the fractional distillation of a $C_3$-$C_{20}$-aldehyde mixture for providing the hydrogenation feed. The heat-consuming step is especially the fractional distillation of a $C_3$-$C_{20}$-aldehyde mixture which comprises at least two $C_3$-$C_{20}$-alkanals having the same number of carbon atoms. As explained in more detail below, such aldehyde mixtures can be obtained by hydroformylation of the corresponding olefins comprising one less carbon atom.

The stream S1) is preferably recirculated to the hydrogenation zone without removal of a material component. This means that no material component, e.g. in the form of products, starting materials, etc., is separated off from the stream S1) taken off from the hydrogenation zone before this stream is recirculated to the hydrogenation zone.

The stream S1) recirculated to the hydrogenation zone preferably has a temperature which is from about 3 to 30° C. below, preferably from 5 to 25° C. below, the temperature in the reaction zone.

The stream S2) is preferably taken off in gaseous form and condensed during the heat exchange. In this way, the heat of condensation can advantageously be utilized for heat integration.

The stream S3) is preferably recirculated to the hydrogenation zone without removal of a material component. This means that no material component, e.g. in the form of products, starting materials, etc., is separated off from the stream S3) taken off in the hydrogenation of the product of the enalization reaction before this stream is recirculated to the hydrogenation zone.

The stream S3) recirculated to the hydrogenation of the product of the enalization reaction preferably has a temperature which is from about 3 to 30° C. below, preferably from 5 to 25° C. below, the temperature in the reaction zone.

Hydrogenation Feed

The hydrogenation feed comprising at least one $C_3$-$C_{20}$-aldehyde is preferably introduced in liquid form into the hydrogenation zone.

The hydrogenation feed can comprise one aldehyde or a plurality of aldehydes.

The aldehydes to be hydrogenated are preferably aliphatic $C_3$-$C_{20}$-aldehydes, in particular $C_3$-$C_{15}$-aldehydes. The aldehydes can be straight-chain or branched and additionally comprise double bonds in the molecule. The aldehydes which can be used in the process of the invention are in principle not subject to any restrictions.

The $C_3$-$C_{20}$-aldehyde is preferably selected from among propionaldehyde, n-butyraldehyde, isobutyraldehyde, pentanal, hexanal, heptanal, 2-ethylhexanal, 2-ethylhexenal, nonanal, nonenal, decanal, decenal and the hydroformylation products of propylene trimer, propylene tetramer, butene dimer or butene trimer.

The $C_3$-$C_{20}$-aldehyde is particularly preferably selected from among n-butyraldehyde, isobutyraldehyde and mixtures thereof. In particular, n-butyraldehyde is used.

If desired, the aldehydes can be used as solution in an inert diluent. Suitable inert diluents are, for example, hydrocarbons, ethers such as diethyl ether or alcohols. Particular preference is given to using alcohols as diluents, in particular the alcohol which is the hydrogenation product of the aldehyde to be hydrogenated. In a specific embodiment, part of the discharge from the hydrogenation zone is for this purpose recirculated and mixed with the hydrogenation feed. If used, the inert diluent is preferably used in an amount of from 0.1 to 100 parts by weight, in particular from 1 to 50 parts by weight and particularly preferably from 5 to 20 parts by weight, based on one part by weight of aldehyde used.

The hydrogenation feed can comprise traces of water, e.g. in the order of magnitude of from 1 ppm to 4% by weight, which have been introduced via the starting materials in the preceding stages of the synthesis, being formed by condensation reactions or being deliberately added to the hydrogenation feed. These traces of water are not critical to the process of the invention, especially as long as the water remains dissolved in the organic phase.

Hydroformylation

The provision of $C_3$-$C_{20}$-aldehydes for the process of the invention is preferably effected by hydroformylation of corresponding $C_2$-$C_{19}$-olefin starting materials. Such processes are known to those skilled in the art. Thus, for example, EP 0 648 730 A1 describes the preparation of hydroformylation products of propene, in which a propene stream is fed together with carbon monoxide and hydrogen into a hydroformylation reactor and reacted in the presence of a hydroformylation catalyst.

Suitable hydroformylation catalysts are likewise known to those skilled in the art. The hydroformylation is preferably carried out using a rhodium complex catalyst which has one or more organophosphorus compound(s) as ligands and is homogeneously soluble in the reaction medium of the hydroformylation reaction. Suitable ligands are phosphine ligands from the class of triarylphosphines, $C_1$-$C_6$-alkyldiarylphosphines and arylalkyldiphosphines, in particular triphenylphosphine. Further suitable rhodium complex catalysts having sterically hindered phosphite ligands are described, for example, in U.S. Pat. No. 4,668,651, U.S. Pat. No. 4,748,261, U.S. Pat. No. 4,769,498, U.S. Pat. No. 4,774,361, U.S. Pat. No. 4,835,299, U.S. Pat. No. 4,885,401, U.S. Pat. No. 5,059,710, U.S. Pat. No. 5,113,022, U.S. Pat. No. 5,179,055, U.S. Pat. No. 5,260,491, U.S. Pat. No. 5,264,616, U.S. Pat. No. 5,288,918, U.S. Pat. No. 5,360,938, EP-A 472 071 and EP-A 518 241.

The hydroformylation product can be separated off from the discharge from the reaction zone in various ways. It is possible to use, for example, a hydroformylation process with liquid discharge as described, for example, in U.S. Pat. No. 4,148,830, EP-A 16 286, EP-A 188 246 or EP-A 423 769. Preference is given to a liquid discharge process in which the essentially, except for the synthesis gas used in excess for the hydroformylation, liquid discharge from the reaction zone is depressurized and separated, as a result of the reduction in pressure in the discharge, into a liquid phase consisting essentially of high-boiling by-products, the homogeneously dissolved hydroformylation catalyst, part of the hydroformylation product and dissolved, unreacted propylene and propane and a gas phase consisting essentially of hydroformylation product, unreacted propylene and propane and also unreacted carbon monoxide and hydrogen and inerts (e.g. $N_2$, $CO_2$, methane). The liquid phase can, optionally after further removal of product aldehydes comprised therein, be recirculated as recycle stream to the reactor. At least partial condensation of the gas phase gives the crude hydroformylation product. The gas phase remaining after the condensation is entirely or partly recirculated to the reaction zone. The gas and liquid phases initially obtained in the depressurization stage can advantageously be worked up by the process described in WO 97/07086. For this purpose, the liquid phase is heated and introduced into the upper region of a column, while the gas phase is introduced into the bottom of the column. Liquid phase and gas phase are thereby conveyed in countercurrent. As a result of the intimate contact of the gas phase with the liquid phase, the residual amounts of hydroformylation product, unreacted propylene and propane present in the liquid phase are transferred to the gas phase, so that the gas stream leaving the column at the top is enriched in hydroformylation product and unreacted propylene and propane, compared to the gas stream introduced at the lower end of the column.

As an alternative, it is possible to employ the gas recycle process in which a gas stream is taken off from the gas space of the hydroformylation reactor. This gas stream consists essentially of synthesis gas, unreacted propylene and propane, with, depending on the vapor pressure in the hydroformylation reactor, the hydroformylation product formed in the hydroformylation reaction being entrained. The entrained crude hydroformylation product is condensed out from the gas stream, e.g. by cooling, and the gas stream which has been freed of the liquid component is recirculated to the hydroformylation reactor. The unreacted propylene and propane comprised in dissolved form in the crude hydroformylation product which has been condensed out can then, as described, be liberated in, for example, a degassing column.

Aldehyde Distillation

In the preparation of aldehydes by hydroformylation, product mixtures which comprise at least two isomeric aldehydes having the same number of carbon atoms are frequently obtained. However, an isomer mixture is frequently undesirable for the further use of the saturated $C_3$-$C_{20}$-alcohols obtained by the process of the invention. This applies particularly when an n-butyraldehyde/isobutyraldehyde mixture from hydroformylation of propene is used for providing the hydrogenation feed and part of the n-butyraldehyde is to be further processed to give 2-ethylhexanol in an integrated process. Here, the use of aldehyde mixtures comprising isobutyraldehyde is undesirable since isobutyraldehyde leads to the formation of 2-ethyl-4-methylpentanol which cannot be separated off economically from 2-ethylhexanol by distillation.

In many cases, the isomeric $C_3$-$C_{20}$-aldehydes can be separated more easily than the isomeric $C_3$-$C_{20}$-alcohols obtained therefrom after the hydrogenation. This applies especially to mixtures of n-butyraldehyde and isobutyraldehyde, as comparison of the boiling points under standard conditions shows: n-butyraldehyde: 75° C., isobutyraldehyde: 63° C., n-butanol: 117.7° C., isobutanol (2-methyl-1-propanol): 108° C.

The advantage of hydrogenation using a distilled aldehyde feed is essentially also the lower by-product formation and longer catalyst operation life in the hydrogenation.

In a preferred embodiment of the process of the invention, an aldehyde mixture comprising at least two $C_3$-$C_{20}$-aldehydes having the same number of carbon atoms is therefore subjected to fractional distillation to give a fraction comprising the major part of one of the $C_3$-$C_{20}$-aldehydes and this fraction is then used as hydrogenation feed.

If desired, the fractional distillation is carried out to give at least two fractions which each comprise the major part of one of the isomeric $C_3$-$C_{20}$-aldehydes. It is then possible to subject only one or a plurality of these fractions, in each case separately, to hydrogenation and fractional distillation according to the process of the invention. It is in this case possible to take off a stream S1) and/or a stream S2) either only in the hydrogenation and distillation of one of the isomeric aldehydes or in the hydrogenation and distillation of a plurality of the isomeric aldehydes. The streams S1) and S2) can, independently of one another, transfer heat to the same or different streams to be heated. In a specific embodiment, all streams S1) and S2) taken off are used for heating the aldehyde mixture to be fractionally distilled.

In an especially preferred embodiment of the process of the invention, an n-butyraldehyde/isobutyraldehyde mixture is subjected to fractional distillation to give a fraction comprising the major part of the n-butyraldehyde and a fraction comprising the major part of the isobutyraldehyde and the fraction comprising the major part of the n-butyraldehyde or the fraction comprising the major part of the isobutyraldehyde is used as hydrogenation feed.

It is of course likewise possible to subject both the n-butyraldehyde-comprising fraction and the isobutyraldehyde-comprising fraction to hydrogenation and fractional distillation according to the process of the invention in each case. It is here possible to take off a stream S1) and/or a stream S2) either only in the hydrogenation and distillation of n-butyraldehyde or only in the hydrogenation and distillation of isobutyraldehyde or to take off a stream S1) and/or a stream S2) both in the hydrogenation and distillation of n-butyraldehyde and in the hydrogenation and distillation of isobutyraldehyde. The streams S1) and S2) can, independently of one another, transfer heat to the same or different streams to be heated. In a specific embodiment, all streams S1) and S2) taken off are used for heating the aldehyde mixture to be fractionally distilled.

In a further preferred embodiment, the fraction comprising the major part of the n-butyraldehyde is divided into two subfractions, the first subfraction is subjected to hydrogenation and distillation, the second subfraction is subjected to an enalization reaction, the product obtained in the enalization reaction is catalytically hydrogenated, a liquid stream S3) is taken off in the hydrogenation of the product of the enalization reaction and heat is withdrawn from this stream S3) by indirect heat exchange and used in the fractional distillation of the n-butyraldehyde/isobutyraldehyde mixture. In this specific embodiment, the heat of hydrogenation from the 2-ethylhexenal hydrogenation and the heat of hydrogenation from the butanol hydrogenations is thus transferred to the aldehyde separation column. The 2-ethylhexenal hydrogenation is preferably carried out using three hydrogenation reactors which are connected in series and all three of which are within the integrated heat system according to the invention.

The fractional distillation of the aldehyde mixture can in principle be carried out by customary distillation processes known to those skilled in the art. Suitable apparatuses for the fractional distillation comprise distillation columns, e.g. tray columns, which can be provided with bubble caps, sieve plates, sieve trays, packings, internals, valves, side offtakes, etc. Thermally coupled columns and dividing wall columns which can be provided with side offtakes, recirculations, etc., are especially suitable. A combination of two or more than two distillation columns can be used for the distillation. Further suitable apparatuses are evaporators such as thin film evaporators, falling film evaporators, Sambay evaporators, etc., and combinations thereof.

In a specific embodiment, an n-butyraldehyde/isobutyraldehyde-comprising mixture is subjected to fractional distillation. This mixture is especially a crude n-butyraldehyde/isobutyraldehyde-comprising mixture from the hydroformylation of propene, which can comprise a major part of butyraldehydes and optionally also further components. The crude butyraldehyde-comprising mixture preferably has a proportion of n-butyraldehyde and isobutyraldehyde of at least 80% by weight, preferably at least 90% by weight, in particular at least 95% by weight, based on the total weight of the mixture. The further components comprise butanols and high-boiling components, e.g. products of aldol condensation.

An especially suitable process for the fractional distillation of a liquid crude aldehyde mixture is described in WO 00/58255 (BASF), which is hereby fully incorporated by reference.

Subsequently, a crude aldehyde mixture comprising a straight-chain aldehyde and at least one branched aldehyde is subjected to fractional distillation, wherein:
A) the crude aldehyde mixture is fed into the middle region of a first distillation column having a plurality of theoretical plates and a separation into
  i) a first aldehyde product stream which is taken off at or close to the top of the distillation column and comprises essentially pure branched aldehyde,
  ii) a second aldehyde product stream which is taken off directly above the vaporizer or higher up in the region of the first 20% of the total theoretical plates and comprises essentially pure straight-chain aldehyde and
  iii) a further product stream comprising high boilers and straight-chain aldehyde
  is carried out therein and
B) the further product stream is fed into a second distillation column and separated therein into an aldehyde product stream which comprises essentially purified straight-chain aldehyde and is taken off at the top or close to the top of the distillation column and a high-boiler stream.

The aldehyde product stream obtained in the second distillation column is preferably recirculated to the first distillation column.

The product stream comprising the constituents having boiling points higher than that of the straight-chain aldehyde which is obtained in the second distillation column is preferably taken off at the bottom of the second distillation column. This stream can be passed to thermal utilization. The quantity of heat obtained here can, for example, be utilized for steam generation and be used in a heat-consuming step of the process of the invention and especially for heating the aldehyde mixture to be fractionally distilled.

The fractional distillation of an aldehyde mixture comprising at least two $C_3$-$C_{20}$-aldehydes having the same number of carbon atoms and especially the fractional distillation of an n-butyraldehyde/isobutyraldehyde mixture is one of the important heat-consuming steps of the process of the invention. For this reason, heat from the streams S1) and/or S2) is preferably transferred to the aldehyde mixture to be fractionated. For this purpose, a stream S1) or S2) can be conveyed through a heat exchanger which serves as vaporizer of the separation column. In a suitable embodiment, a plurality of streams S1) and/or S2) are used for heating the aldehyde mixture. These streams can be, for example, two or more than two streams S1) from different hydrogenation reactions, e.g. the hydrogenation of n-butyraldehyde and the hydrogenation of isobutyraldehyde. Furthermore, these streams can be, for example, two or more than two streams S2) from different distillations, e.g. the distillation of n-butanol and the distillation of isobutanol. Furthermore, it is also possible to use at least one steam S1) and at least one stream S2) for heating the aldehyde mixture. If a plurality of streams are used for heating the aldehyde mixture, heating can be carried out in one heat exchanger or a plurality of separately constructed heat exchangers. The spatial arrangement and configuration of the exchange surfaces in contact with the individual streams S1) and S2) and their order within the heat exchanger (or in the case of the use of a plurality of heat exchangers, their design and order) is carried out, inter alia, as a function of the temperature difference between the stream S1) or S2) used for heat exchange and the aldehyde stream.

If a plurality of distillation columns are used for the fractional distillation of the aldehyde mixture, the streams S1) and S2) can be used for heating the feed stream to any of the distillation columns. A plurality of streams S1) and S2) can be used for heating the feed stream to only one of the distillation columns or a plurality of the distillation columns.

To supply the energy necessary for the fractional distillation, each distillation column can be additionally equipped with conventional heating, e.g. by means of steam.

Hydrogenation

In the hydrogenation, the $C_3$-$C_{20}$-aldehyde and the resulting $C_3$-$C_{20}$-alcohol are preferably present in the liquid phase.

The temperature in the hydrogenation is preferably from 50 to 300° C., in particular from 100 to 250° C.

The reaction pressure in the hydrogenation is preferably from 5 bar to 300 bar, in particular from 10 to 150 bar.

The hydrogen-comprising gas used for the hydrogenation preferably comprises more than 80 mol % of hydrogen. In particular, it consists essentially of hydrogen. The hydrogen-comprising gas can be conveyed in concurrent or countercurrent with/to the hydrogenation feed. It is preferably conveyed in concurrent. The amount of hydrogen-comprising gas introduced is advantageously such that from 1.0 to 1.15 times the stoichiometrically required amount of hydrogen is available.

As hydrogenation catalyst, use is made of the catalysts usually employed for the hydrogenation of aldehydes to alcohols. The type of catalyst used is not subject matter of the present invention; the advantageous effects achieved by means of the process of the invention are generally independent of the type of hydrogenation catalyst used. Accordingly, it is possible to use many hydrogenation catalysts, for example metal-comprising supported catalysts having metals of transition groups I, VII and/or VIII of the Periodic Table as catalytically active components, in particular supported catalysts having rhenium, platinum, palladium, rhodium and/or ruthenium as catalytically active components and support materials such as aluminum oxide, titanium dioxide, silicon dioxide, zirconium dioxide, barium sulfate; or precipitated catalysts comprising at least one element of transition groups I, VI, VII and/or VIII of the Periodic Table, for example the catalysts as are described in DE-A 32 28 881, DE-A 26 28 987 and DE-A 24 45 303, in the process of the invention. Preferred hydrogenation catalysts are modified Adkins catalysts as are described in J. Am. Chem. Soc. 51, 2430 (1929) and J. Am. Chem. Soc. 54, 4678 (1932). A preferred hydrogenation catalyst in the unreduced state comprises 35% by weight of copper, calculated as Cu, 31% by weight of chromium, calculated as Cr, 2.0% by weight of barium, calculated as Ba, and 2.5% by weight of manganese, calculated as Mn. Further preferred hydrogenation catalysts are catalysts according to DE-A 26 28 98. A preferred hydrogenation catalyst in the unreduced state comprises 24% by weight of nickel, calculated as NiO, 8% by weight of copper, calculated as CuO, 2.0% by weight of manganese, calculated as MnO, on 66% by weight of $SiO_2$ as support material. The catalysts are preferably present in particulate form and generally have a particle size of from 3 to 10 mm.

The hydrogenation is preferably carried out continuously. The hydrogenation zone can comprise a single reactor or a plurality of hydrogenation reactors. In a specific embodiment of the process of the invention, the hydrogenation feed is subjected to continuous hydrogenation in at least two (e.g.

two, three or more than three) hydrogenation reactors connected in series. The hydrogenation is preferably carried out in a combination of two hydrogenation reactors. This allows particularly advantageous removal of the heat of hydrogenation evolved.

This in turn allows very complete hydrogenation of the aldehydes used together with good selectivity to the desired alcohol.

If the hydrogenation is carried out continuously in at least two reactors connected in series, each reactor can have one or more reaction zones within the reactor. The reactors can be identical or different reactors. These can, for example, have identical or different mixing characteristics and/or be divided in one or more places by intervals. Suitable pressure-rated reactors for the hydrogenation are known to those skilled in the art. They include the generally customary reactors for gas-liquid reactions, e.g. tube reactors, shell-and-tube reactors, gas circulation reactors, bubble columns, loop apparatuses, stirred vessels (which can also be configured as cascades of stirred vessels), air-lift reactors, etc.

The various reactors can be operated in the fixed-bed or suspension mode. The fixed-bed mode is preferred. The catalysts can be arranged in one or more beds in the reactor. Different catalysts can be used in the various beds of a reactor or the various reactors of a reactor cascade.

If the hydrogenation is carried out in at least two hydrogenation reactors connected in series, the first hydrogenation reactor preferably has a stream conveyed in an external circuit (external circulation stream, liquid circuit). The reaction in the last of the reactors connected in series is preferably carried out adiabatically. For the process of the present invention, this term is used in the industrial and not physicochemical sense. Thus, the reaction mixture generally experiences an increase in temperature because of the exothermic hydrogenation reaction while flowing through the last reactor. For the purposes of the invention, an adiabatic reaction is a procedure in which the heat liberated in the hydrogenation is taken up by the reaction mixture in the reactor and no cooling by means of cooling devices is employed. Thus, the heat of reaction is discharged from the last reactor together with the reaction mixture, apart from a residual proportion which is given off to the environment by the reactor by means of natural thermal conduction and thermal radiation. The last reactor is preferably operated in a single pass.

In a preferred embodiment, two fixed-bed reactors connected in series are used for the hydrogenation. The first hydrogenation reactor then preferably has a stream conveyed in an external circuit. Furthermore, the reaction in the second reactor is preferably carried out adiabatically. The second reactor is preferably operated in a single pass.

Another preferred variant is carrying out the hydrogenation of 2-ethylhexenal using three hydrogenation reactors connected in series in a joint circulation circuit without an adiabatic after-reactor.

According to the invention, a hot stream is taken off either from the hydrogenation zone (=stream S1)) or at the top of a distillation column of the subsequent alcohol distillation (=stream S2)) or from the hydrogenation zone and the distillation column and heat is withdrawn from this stream by indirect heat exchange and transferred to a stream to be heated.

The stream S1) and the discharge for the distillation can be taken off separately or in a joint stream from the hydrogenation zone.

In a preferred embodiment, two reactors connected in series are used for the hydrogenation. Preference is then given to taking off the stream S1) from the first reactor and the feed for the second reactor in a joint stream. Heat is preferably firstly withdrawn from the joint stream. Subsequently, the joint stream is then divided, a first substream is recirculated to the first reactor and a second substream is fed as feed to the second reactor. The ratio of recirculated stream to stream fed to the second reactor is preferably from 50:1 to 5:1. If desired, it is also possible to take off a stream S1) from the second reactor and withdraw heat from this. Preference is then given to taking off the stream S1) from the second reactor and the discharge for the distillation in a joint stream. In a specific embodiment, no stream S1) is taken off from the second reactor.

In the hydrogenation according to the process of the invention, the aldehydes are converted in high yields and with high selectivity into the corresponding alcohols.

The hydrogenation discharge consists essentially of the $C_3$-$C_{20}$-alcohols corresponding to the $C_3$-$C_{20}$-aldehydes used. Further constituents are, inter alia, water, di-($C_3$-$C_{20}$-alkyl) ethers, high boilers (e.g. from acetalization, aldolization, Tishchenko reaction), etc. In the following, a distinction is made in respect of the further constituents between low boilers (i.e. components which are more volatile than the $C_3$-$C_{20}$-alcohol obtained as main product in the hydrogenation) and high boilers (i.e. components which are less volatile than the $C_3$-$C_{20}$-alcohol obtained as main product in the hydrogenation).

Alcohol Distillation

The hydrogenation discharge can subsequently be worked up by conventional distillation processes known to those skilled in the art.

Suitable apparatuses for the work-up by distillation comprise distillation columns, e.g. tray columns, which can be provided with bubble caps, sieve plates, sieve trays, packings, internals, valves, side offtakes, etc. Especially suitable columns are dividing wall columns which can be provided with side offtakes, recirculations, etc. The distillation can be carried out using a combination of two or more than two distillation columns. Further suitable apparatuses are evaporators such as thin film evaporators, falling film evaporators, Sambay evaporators, etc., and combinations thereof.

In a preferred embodiment, the discharge from the hydrogenation zone is firstly subjected to degassing. For this purpose, the discharge can, optionally after cooling, be transferred to a suitable vessel and the gas phase can be separated off. This can, for example, be passed to thermal utilization. The degassed hydrogenation discharge is then used for the fractional distillation.

In a specific embodiment, the fractional distillation is carried out by means of rectification, in which
  i) the discharge for the hydrogenation zone is, optionally after gaseous components have been separated off, introduced at the side into a first distillation column,
  ii) the low boilers are taken off at the top of the first distillation column,
  iii) the bottoms from the first distillation column are introduced at the side into a second distillation column,
  iv) a gaseous discharge is taken off at the top of the second distillation column, heat is withdrawn from this as stream S2), resulting in a phase separation into a gas phase and a liquid phase occurring, the gas phase is discharged and the liquid phase is partly recirculated to the top region in the second distillation column and partly fed at the side into the first distillation column, v) the purified $C_3$-$C_{20}$-alcohol is taken off from the second distillation column at the side above the feed point for the bottoms from the first distillation column and below the top,
vi) a fraction comprising the high boilers is taken off at the bottom of the second distillation column,
vii) the bottoms from the second distillation column are optionally subjected to further fractionation.

Preparation of 2-Ethylhexanol

In a specific embodiment of the process of the invention, an n-butyraldehyde-comprising fraction is subjected to an enalization reaction, the product mixture obtained in the enalization reaction is catalytically hydrogenated and the hydrogenation product is subjected to distillation to give a fraction enriched in 2-ethylhexanol. Such processes are known to those skilled in the art and are described, for example, in U.S. Pat. No. 5,227,544, which is hereby fully incorporated by reference.

The invention is illustrated by the following, nonlimiting examples.

EXAMPLES

Comparative Example 1

Hydrogenation of n-Butyraldehyde

A 40 m³ reactor into which a feed composed of liquid n-butyraldehyde and pure hydrogen was used for the hydrogenation. The n-butyraldehyde was obtained in a distillation column by separation of a crude aldehyde mixture into the pure components n-butyraldehyde and isobutyraldehyde. The steam consumption of the butyraldehyde column is from 20 to 30 metric t/h. 10 metric t/h of n-butyraldehyde and 400 kg/h of hydrogen were continuously fed as starting materials into the hydrogenation reactor. The cooling of the hydrogenation reactor was effected in an external cooling circuit via which the heat of reaction of the hydrogenation is transferred to air and cooling water. The temperature of the discharge stream is 135° C. at the outlet of the reactor and 115° C. on re-entry into the reactor.

Example 2

In a reactor as per example 1, the heat of reaction of the hydrogenation of n-butyraldehyde was utilized as one of the energy sources for the butyraldehyde separation column by passing the external cooling circuit through one of the vaporizers of the separation column. The resulting saving of steam is 4.2 metric t/h.

Comparative Example 3

Hydrogenation of 2-Ethylhexenal

A reactor system into which a feed composed of 10 metric t/h of liquid 2-ethylhexenal and 400 of pure hydrogen was used for the hydrogenation. The cooling of the hydrogenation reactor was effected in an external cooling circuit via which the heat of reaction of the hydrogenation is transferred to air and cooling water. The temperature of the discharge stream is 170° C. at the outlet of the reactor and 122° C. on re-entry into the reactor.

Example 4

The reaction of comparative example 3 was carried out in a reactor as per example 1 and the heat of reaction of the hydrogenation of 2-ethylhexenal was utilized as one of the energy sources for the butyraldehyde separation column by passing the external cooling circuit through one of the vaporizers of the separation columns. The resulting saving of steam is 5.5 metric t/h.

Comparative Example 5

Pure Distillation of n-Butanol

A distillation column into which a feed composed of a crude alcohol which has previously been freed of low boilers is used for the production of pure n-butanol. A feed rate of 10 metric t/h typically requires a steam flow of 4.7 metric t/h. The energy fed in this way into the column is essentially withdrawn again via the overhead condenser and transferred to a cooling medium. Depending on the design of the column, this can be carried out by means of an air condenser or a water condenser.

Example 6

On a distillation column as per example 5, the heat of condensation of the n-butanol distillation is utilized as one of the energy sources for the butyraldehyde separation column by introducing the vapor from the distillation column directly into one of the vaporizers of the separation column and condensing it there. The resulting saving of steam is 4.5 metric t/h.

The invention claimed is:

1. A process for heat integration in the preparation of saturated C3-C20-alcohols, in which a hydrogenation feed comprising at least one C3-C20-aldehyde is hydrogenated in the presence of a hydrogen-comprising gas in a hydrogenation zone and a discharge is taken off from the hydrogenation zone and subjected to distillation in at least one distillation column to give a fraction which is enriched in saturated C3-C20-alcohols, wherein
   a liquid stream S1) is taken off from the hydrogenation zone, heat is withdrawn from this stream and the stream is subsequently recirculated to the hydrogenation zone and/or
   a gaseous stream S2) is taken off at the top of at least one distillation column, heat is withdrawn from this stream and the stream is optionally then recirculated to the distillation,
where the heat is withdrawn from the stream S1) and/or the stream S2) by indirect heat exchange and is transferred to a stream to be heated without the use of an auxiliary medium for heat transfer,
wherein an aldehyde mixture comprising at least two $C_3$-$C_{20}$-aldehydes having the same number of carbon atoms is subjected to fractional distillation to give a fraction comprising the major part of one of the $C_3$-$C_{20}$-aldehydes and this fraction is used as hydrogenation feed, and
wherein heat withdrawn from the stream S1) and/or the heat withdrawn from the stream S2) is used for heating the aldehyde mixture to be fractionally distilled.

2. The process according to claim 1, wherein the $C_3$-$C_{20}$-aldehyde is selected from among propionaldehyde, n-butyraldehyde, isobutyraldehyde, pentanal, hexanal, heptanal, 2-ethylhexanal, 2-ethylhexenal, nonanal, nonenal, decanal, decenal and the hydroformylation products of propylene trimer, propylene tetramer, butene dimer or butene trimer.

3. The process according to claim 1, wherein the $C_3$-$C_{20}$-aldehyde is selected from among n-butyraldehyde, isobutyraldehyde and mixtures thereof.

4. The process according to claim 1, wherein the provision of the $C_3$-$C_{20}$-aldehydes comprises the hydroformylation of an olefin starting material.

5. The process according to claim 1, wherein an n-butyraldehyde/isobutyraldehyde mixture is subjected to fractional distillation to give a fraction comprising the major part of the n-butyraldehyde and a fraction comprising the major part of the isobutyraldehyde and the fraction comprising the major part of the n-butyraldehyde and/or the fraction comprising the major part of the isobutyraldehyde is used as hydrogenation feed.

6. The process according to claim 5, wherein the fraction comprising the major part of the n-butyraldehyde is divided into two subtractions, the first subfraction is hydrogenated in the presence of a hydrogen-comprising gas in a hydrogenation zone, a discharge is taken off from the hydrogenation zone and subjected to a distillation in at least one distillation column to give a fraction enriched in n-butanol and the second subfraction is subjected to an enalization reaction, the product mixture obtained in the enalization reaction is catalytically hydrogenated and the hydrogenation product is subjected to a distillation to give a fraction enriched in 2-ethylhexanol.

7. The process as claimed in claim 6, wherein a liquid stream S3) is taken off in the hydrogenation of the product of the enalization reaction, heat is withdrawn from this stream S3) by indirect heat exchange and transferred to a stream to be heated without the use of an auxiliary medium for heat exchange and the stream S3) is subsequently recirculated to the hydrogenation of the product of the enalization reaction.

8. The process according to claim 1, wherein the heat withdrawn from the stream S1) and/or the heat withdrawn from the stream S2) and/or the heat withdrawn from the stream S3) is used for heating a stream in the preparation of the saturated $C_3$-$C_{20}$-alcohols.

9. The process according to claim 7, wherein the heat withdrawn from the stream S1) and/or the heat withdrawn from the stream S2) and/or the heat withdrawn from the stream S3) is used for heating the aldehyde mixture to be fractionally distilled.

10. The process according to claim 1, wherein the stream S1) and/or the stream S3) is recirculated without removal of a material component to the hydrogenation zone.

11. The process according to claim 1, wherein the stream S2) is condensed in the heat exchange.

12. A process for heat integration in the preparation of n-butanol and/or isobutanol, wherein
  a) an n-butyraldehyde/isobutyraldehyde mixture is subjected to fractional distillation to give a fraction comprising the major part of the n-butyraldehyde and a fraction comprising the major part of the isobutyraldehyde,
  b1) the stream comprising the major part of the n-butyraldehyde from step a) is subjected to hydrogenation in the presence of hydrogen in a hydrogenation zone H1),
  c1) optionally, a liquid stream S1c1) is taken off from the hydrogenation zone H1), heat is withdrawn from this stream by passing it together with the n-butyraldehyde/isobutyraldehyde mixture to be fractionated in step a) through a heat exchanger and subsequently recirculating the stream to the hydrogenation zone H1),
  d1) a discharge is taken off from the hydrogenation zone H1) and subjected to distillation in at least one distillation column to give a fraction enriched in n-butanol,
  e1) optionally, a gaseous stream S2e1) is taken off at the top of at least one of the distillation columns, heat is withdrawn from this stream by passing it together with the n-butyraldehyde/isobutyraldehyde mixture to be fractionated in step a) through a heat exchanger and optionally then recirculating the stream to the distillation, and/or b2) the stream comprising the major part of the isobutyraldehyde from step a) is subjected to hydrogenation in the presence of hydrogen in a hydrogenation zone H2),
  c2) optionally, a liquid stream S1c2) is taken off from the hydrogenation zone H2), heat is withdrawn from this stream by passing it together with the n-butyraldehyde/isobutyraldehyde mixture to be fractionated in step a) through a heat exchanger and subsequently recirculating the stream to the hydrogenation zone H2),
  d2) a discharge is taken off from the hydrogenation zone H2) and subjected to distillation in at least one distillation column to give a fraction enriched in isobutanol,
  e2) optionally, a gaseous stream S2e2) is taken off at the top of at least one of the distillation columns, heat is withdrawn from this stream by passing it together with the n-butyraldehyde/isobutyraldehyde mixture to be fractionated in step a) through a heat exchanger and optionally then recirculating the stream to the distillation,
  with the proviso that at least one of the steps c1), e1), c2) or e2) is necessarily provided.

13. The process according to claim 12, wherein, in step a), the fraction comprising the major part of the n-butyraldehyde is at least partly subjected to an enalization reaction, the product mixture obtained in the enalization reaction is catalytically hydrogenated and the hydrogenation product is subjected to a distillation to give a fraction enriched in 2-ethylhexanol.

14. The process according to claim 13, wherein a liquid stream S3) is taken off in the hydrogenation of the product of the enalization reaction, heat is withdrawn from this stream S3) by passing it together with the n-butyraldehyde/isobutyraldehyde mixture to be fractionated in step a) through a heat exchanger and the stream S3) is subsequently recirculated to the hydrogenation of the product of the enalization reaction.

\* \* \* \* \*